United States Patent [19]

Schertl et al.

[11] Patent Number: 5,668,230
[45] Date of Patent: *Sep. 16, 1997

[54] OLEFIN POLYMERIZATION

[75] Inventors: Peter Schertl, Neuhaus a. d. Pegnitz; Helmut G. Alt, Bayreuth, both of Germany; M. Bruce Welch, Bartlesville, Okla.

[73] Assignee: Phillips Petroleum Company, Bartlesville, Okla.

[*] Notice: The term of this patent shall not extend beyond the expiration date of Pat. No. 5,436,305.

[21] Appl. No.: 678,281

[22] Filed: Jul. 11, 1996

Related U.S. Application Data

[63] Continuation-in-part of Ser. No. 192,223, Feb. 3, 1994, Pat. No. 5,571,880, and Ser. No. 352,936, Dec. 9, 1994, which is a division of Ser. No. 734,853, Jul. 23, 1991, Pat. No. 5,436,305.

[51] Int. Cl.$^6$ .............................. C08F 4/64; C08F 10/02
[52] U.S. Cl. .......................... 526/160; 526/132; 526/170; 526/352; 526/943; 502/103; 502/117; 502/152
[58] Field of Search ..................... 526/160, 170, 526/132, 943; 502/117, 152, 103, 153, 154; 556/52

[56] References Cited

U.S. PATENT DOCUMENTS

| | | | |
|---|---|---|---|
| 3,205,257 | 9/1965 | Fritz et al. | 260/465 |
| 5,079,260 | 1/1992 | Weitzberg et al. | 514/532 |
| 5,391,789 | 2/1995 | Rohrmann | 556/11 |
| 5,571,880 | 11/1996 | Alt et al. | 526/943 X |

FOREIGN PATENT DOCUMENTS 577581  1/1994  European Pat. Off. .

*Primary Examiner*—Fred Teskin
*Attorney, Agent, or Firm*—Edward L. Bowman

[57] ABSTRACT

A catalyst system and process for polymerizing olefins employing a cocatalyst and specific ethylene bridged fluorenyl-containing metallocenes having substituents which result in high yields of polyethylene and/or high molecular weight polyethylene.

18 Claims, No Drawings

OLEFIN POLYMERIZATION

This application is a continuation-in-part of application Ser. No. 08/352,936 filed Dec. 9, 1994 which was a divisional of application Ser. No. 07/734,853 filed Jul. 23, 1991, now U.S. Pat. No. 5,436,305. This application is also a continuation-in-part of U.S. patent application Ser. No. 08/192,223 filed Feb. 3, 1994, now U.S. Pat. No. 5,571,880. The disclosures of the aforementioned applications are incorporated herein by reference.

FIELD OF THE INVENTION

The present invention relates to the polymerization of olefins. More specifically, the present invention relates to the polymerization of olefins using a metallocene catalyst system. In another aspect this invention relates to a catalyst system useful in the polymerization of olefins.

BACKGROUND OF THE INVENTION

Recently it has been determined that a variety of different types of bridged metallocenes are suitable for the polymerization of olefins. The metallocenes do not, however, always provide the desired levels of activity or polymers of the desired molecular weight.

An object of the present invention is to provide methods for preparing higher yields of polyolefins and/or higher molecular weight polyolefins.

SUMMARY OF THE INVENTION

In accordance with the present invention there is provided a process for polymerizing olefins. The process involves contacting an olefin with a catalyst system prepared by combining a metallocene and a suitable cocatalyst. The metallocene is selected from ethylene bridged metallocenes of Group IVB metals having two fluorenyl components each bonded at the 9-position to opposite ends of the ethylene bridge. The metallocenes are farther characterized by the fact that at least one of the fluorenyl groups is substituted by either (1) a substituent in the 4-position selected from the group consisting of alkyl, aryl, or aralkyl radicals having 1 to 10 carbon atoms; (2) aryl substituents at the 2- and 7-positions; (3) tertiary-butyl substituents at the 2- and 7-positions; or (4) a 4,5-benzo substituent.

DETAILED DESCRIPTION OF THE INVENTION

The metallocenes can be prepared using the technique disclosed in the above-mentioned U.S. Pat. No. 5,436,305 by reacting the required fluorenyl ethane compound with a transition metal halide. Techniques for producing suitable fluorenyl ethane compounds are disclosed in U.S. Pat. No. 5,191,132 and the aforementioned U.S. patent application Ser. No. 192,223. For example, symmetrical compounds can be obtained by the direct alkylation of the 9-lithium salt of the selected fluorene compound with 1,2-dibromoethane. A preferred technique for preparing unsymmetrical fluorenyl ethane compounds involves preparing 1-bromo-2-(9-fluorenyl) ethane and reacting it with the lithium salt of the selected substituted fluorenyl compound.

The substituted fluorene compounds needed to make the ligands for the selected metallocenes can be prepared by various techniques. Some examples are disclosed in the aforementioned U.S. patent application Ser. No. 192,223. The compound 2,7-di(1-naphthyl)fluorene, also known as 2,7-di(1-naphthyl)-9H-fluorene, can be prepared using cross coupling of 2,7-diiodide-9H-fluorene with 1-naphthylmagnesium bromide in diethyl ether using bis (triphenylphosphine)nickel dichloride as a catalyst. The compound 2,7-diphenylfluorene can be prepared in a similar manner using phenylmagnesium bromide. The analogus 2-arylfluorenyls can be obtained using 2-iodofluorene as the starting material. The compound 2,7-di-tert-butylfluorene can be obtained from 2,7-diacetyl-9H-fluorene by reaction with trimethyl aluminum. The compound 4-methyl-9H-fluorene can be obtained by the ring closure of diphenic acid followed by reaction with thionyl chloride and cyclization using Friedel-Crafts acylation with aluminum trichloride. The resulting fluoren-9-on-4-carboxylic acid can then be reduced with lithium aluminum hydride and hydrogenated with palladium on carbon to yeild 4-methylfluorene. The compound 4-benzyl-9H-fluorene can be produced by subjecting 4-benzoyl-9H-fluorene to stepwise reduction with lithium aluminum hydride followed by hydrogen iodide in acetic acid. The compound 4,5-benzofluorene can be prepared using the technique disclosed in *Bull. Chem. Soc. Jap.* 56, 2179 (1983).

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of triethylaluminum and dimethylfluoroaluminum such as disclosed by Zambelli et al, *Macromolecules*, 22, 2186 (1989). In such counter anion systems the cocatalyst can be viewed as an ion-exchange compound comprising a cation which will irreversibly react with at least one ligand contained in the metallocene and a non-coordination anion which is either a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

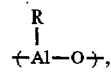

where R is generally a hydrocarbyl group having 1 to 5 carbon atoms.

Aluminoxanes, also sometimes referred to as poly (hydrocarbyl aluminum oxides) are well known in the art and are generally prepared by reacting an hydrocarbylaluminum compound with water. Such a preparation techniques are disclosed in U.S. Pat. Nos. 3,242,099 and 4,808,561, the disclosures of which are incorporated herein by reference. The currently preferred aluminoxane cocatalysts are prepared either from methylaluminum or triethylaluminum and are sometimes referred to as poly(methyl aluminum oxide)

and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the bridged sandwich bonded fluorenyl metallocene is employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique of producing a solid cocatalyst involves contacting an organoaluminoxane with an organic borane compound free of acidic hydrogen as taught in pending U.S. patent application Ser. No. 08/080,899 filed Jun. 22, 1993, now allowed, the disclosure of which is incorporated herein by reference. Yet another technique involves contacting an organoaluminoxane with an organoboron compound having boron acid functionality, i.e. —BOH, as taught in pending U.S. patent application Ser. No. 08/092,143 filed Jul. 14, 1993, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in copending U.S. patent application No. 08/017,207 fled Feb. 12, 1993, the disclosure of which is incorporated herein by reference.

Various boroxines are known in the art. The term organo boroxine as used herein refers to compounds of the formula $(RBO)_3$ wherein each R is the same or a different organo group free of hydroxyl (HO—) or mercapto (HS—) groups. The R groups could include such radicals as methyl, ethyl, isopropyl, tertiary butyl, 2-ethyl ethylene, tri-n-butylmethyl, o-tolyl, phenyl, o-tri-fluoromethyl phenyl, o-chloro-phenyl, 2,6-dimethyl phenyl, $C_2H_5$—$CH_2CH_2CH_2$—, $CH_2$=CH—$CH_2$—, α-naphthyl, β-naphthyl, and the like. The R groups could also be R'O—, R'S—, $R_2'N$—, $R_2'P$—, and $R_3'Si$— wherein each R' is a hydrocarbyl group. Generally each R group contains about 1 to about 25 carbon atoms, more typically 1 to 10 carbon atoms. Especially preferred are the hydrocarbyl boroxines and the hydrocarbyloxy boroxines. Examples of hydrocarbyl boroxines include trimethyl boroxine, triethyl boroxine, tri-n-propyl boroxine, tributyl boroxine, tricyclohexyl boroxine, triphenyl boroxine, methyl diethyl boroxine, dimethylethyl boroxine, and the like. The currently preferred hydrocarbyl boroxines are trimethyl boroxine and triethyl boroxine. The term hydrocarbyloxy boroxine refers to compounds of the formula $((R'O)BO)_3$ wherein each R' can be the same or different hydrocarbyl group, generally containing about 1 to about 10 carbon atoms. Trialkyloxy boroxines are currently preferred. Trimethoxy boroxine is an example.

The reaction of the boroxine with the aluminoxane can be carried out in any suitable manner. One particularly desirable technique simply involves contacting the two reactants in a suitable liquid diluent. One preferred technique involves contacting a hydrocarbon solution of the aluminoxane with a hydrocarbon solution of the boroxine. Another technique involves contacting a hydrocarbon solution of the aluminoxane with a countersolvent to produce a slurry comprising soluble aluminoxane and insoluble particulate aluminoxane and then contacting the resulting slurry with a solution of the boroxine. It is also within the scope of the present invention to carry out the reaction of the boroxine and the aluminoxane in the presence of a particulate diluent so that the insoluble product becomes deposited upon the particulate diluent. Typical particulate diluents would include such inorganic materials as silica, alumina, aluminum phosphate, silica-alumina, titania, kaolin, fumed silica, and the like.

It is also within the scope of the present invention to prepare the inventive particulate organo-aluminoxy composition and then combine it with a solution of a trialkylaluminum compound, e.g. trimethylaluminum or others of the type mentioned above, and then to contact the resulting slurry with additional boroxine of the type described above. It is believed that this process may provide a method for further increasing the molecular weight of the particulate aluminoxy composition that is initially produced by reacting the aluminoxane with the boroxine. Obviously, such a process could be repeated several times to obtain the desired level of molecular weight, particle size, bulk density, or other characteristic that is desired for a particular application.

The amount of boroxine employed relative to the aluminoxane can vary over a wide range depending upon the particular results desired. A technique which has been used in this invention for reflecting the ratio of boroxine to aluminoxane, involves the use of a calculated amount for the amount of aluminoxy aluminum in the aluminoxane solution. As used herein the term calculated aluminum is the value obtained by using a vacuum to strip the solvent off a known volume of the aluminoxane solution; weighing the recovered solid; and dividing the weight of the solid per milliter by the average molecular weight of the aluminoxy units,

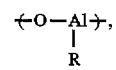

i.e. 58 for methylaluminoxane, so that one obtains a calculated value for the number of moles of aluminum per volume of the aluminoxane solution that is to be reacted with the boroxine. It is theorized that a substantial portion of any free trihydrocarbyl aluminum in the aluminoxane solution is removed when the solvent is stripped off. Any trihydrocarbyl aluminum that is present in the solid recovered after the vacuum stripping, is not considered to have a significant effect upon the calculated aluminum value. Using this method, the atomic ratio of the boron in the boroxine to calculated Al in the aluminoxy units of the aluminoxane employed will be in the range of about 1/20 to about 1/3, more preferably about 1/15 to about 1/5, still more preferably about 1/7. As noted above, the commercial aluminoxane solutions generally contain at least some trihydrocarbyl aluminum, in addition to aluminoxy units. Generally, the trihydrocarbyl aluminum accounts for about about 0.1 to about 35 weight percent of the aluminum in the solution. It is generally preferred for the boroxine to be employed in such an amount that the molar ratio of the boroxine to the trihydrocarbyl aluminum be at least about 0.3334/1.

The metallocene catalyst systems of this invention can be used for the polymerization of olefins having 2 to 12 carbon atoms, especially acyclic olefins, and are particularly useful for the polymerization of ethylene, either alone or with another olefin comomoner. Typically the comonomer is an olefin containing 3 to 30 carbon atoms, more commonly 4 to 12 carbon atoms. Examples of olefin comonomers include propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3,4-dimethyl-1-hexene, and the like and mixtures thereof. The amount of comonomer employed can vary over a wide range depending upon the particular results desired. A particularly interesting type of copolymer is produced when the monomers are employed in amounts such that the molar ratio of the ethylene employed to the comonomer employed is at least about 1 to 1. Interesting copolymers are also obtained when ethylene and an alpha olefin having 4 to 12 carbon atoms are employed in amounts such that the molar ratio of the comonomer employed to the ethylene employed is in the range of about 0.001 to 1 to about 0.5 to 1, more typically in the range of about 0.025/1 to about 0.5/1.

The polymerizations can be carded out under a wide range of conditions depending upon the particular metallocene catalyst system employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

The polymerizations can be carded out using a homogeneous catalyst system in which the catalyst and cocatalyst are soluble; however, it is also within the scope of the present invention to carry out the polymerizations in the presence of solid forms of the catalyst and/or cocatalyst. The metallocene and/or the cocatalyst can be employed on a solid insoluble support, i.e. silica.

When an aluminoxy cocatalyst is employed generally the molar ratio of the aluminum in the organoaluminoxy cocatalyst to the transition metal in the metallocenes would be in the range of about 1:1 to about 100,000:1 and more preferably about 5:1 to about 15,000:1. As a general rule, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about −60° C. to about 300° C., more preferably in the range of about 20° C. to about 160° C. Particularly preferred for slurry or particle form polymerization are temperatures in the range of from about 60° C. to about 120° C. The pressure can also vary over a wide range. Typically the pressure would be in the range of from about 1 to about 500 atmospheres or greater.

The polymers produced with this invention have a wide range of uses that will be apparent to those skilled in the art from the physical properties of the respective polymer. A further understanding of the present invention and its objects and advantages will be provided by a review of the following specific examples.

EXAMPLE I

A series of ethylene polymerizations were conducted in a one liter autoclave type reactor. The ethylene employed was dried over aluminum oxide. First, a catalyst solution was prepared by combining the metallocene and a commercial 30 wt. % toluene solution of methylaluminoxane obtained from Witco to yield a catalyst solution having an Al/Zr molar ratio of 5000/1. The catalyst solution was added to the auto clave that had been filled with 500 ml of n-pentane and 2 ml of the 30 wt. % toluene solution of methylaluminoxane. The resulting mixture was then stirred for one hour at an ethylene pressure of 10 bar at 60° C. The reaction was terminated by releasing the pressure from the reactor. The polymer was recovered and evaluated to determine the viscosity average molecular weight and thermal properties of the polymer. The activity in terms of kg of polyethylene per mmol of metallocene was also determined. The viscosity average molecular weights, i.e. $M_\eta$, in terms of g/mol were determined using a capillary viscometer in cis/trans-decalin at about 135° C. The thermal properties were determined by differential scanning calorimetry. Samples in the amount of 5–10 mg were melted into standard aluminum pans and measured using (1) a heating phase (20 K/min) from 40° C. to 200° C., (2) an isothermal phase of 3 minutes at 200° C., (3) a cooling phase (−20 K/min) to 40° C., (4) a second heating phase (20 K/min) from 40° C. to 200° C. The melting points were determined in the second heating phase. Crystallinity, as indicated by the alpha symbol, was calculated as a percentage of the fusion enthalpy of 100 percent crystalline polyethylene, i.e. 292.9 J/g.

The result of the series of polymerizations are summarized in the following table.

TABLE I

| Run No. | Zirconocene Complex | Activity g PE/ mmol M/hr | $M_\eta$ g/mole | $T_m$, C $\Delta H_m$, J/g $\alpha$, % |
|---|---|---|---|---|
| 1 | 1,2-bis(4,5-dimethyl-fluorenyl)ethane ZrCl$_2$ | 2,601,500 | 440,000 | 135.1 145.8 50 |
| 2 | 1,2-bis(4-methyl-fluorenyl)ethane ZrCl$_2$ | 2,408,000 | 610,000 | 139.4 157.9 54 |
| 3 | 1-(4,5-dimethylfluorenyl)-2-fluorenylethane ZrCl$_2$ | 1,965,000 | 240,000 | 139.7 171.0 58 |
| 4 | 1,2-bis(4-benzyl-fluorenyl)ethane ZrCl$_2$ | 1,464,000 | 610,000 | 139.2 156.2 53 |
| 5 | 1-(3,4-benzofluorenyl)-2-fluorenylethane ZrCl$_2$ | 940,500 | 430,000 | 136.8 163.2 56 |
| 6 | 1-(2,7-dinaphthylfluorenyl)-2- | 693,000 | 760,000 | 139.3 |

TABLE I-continued

| Run No. | Zirconocene Complex | Activity g PE/ mmol M/hr | $M_\eta$ g/mole | $T_m$, C $\Delta H_m$, J/g $\alpha$, % |
|---|---|---|---|---|
| | fluorenylethane $ZrCl_2$ | | | 153.9 53 |
| 7 | 1,2-bis(2,7-dinaphthylfluorenyl)ethane $ZrCl_2$ | 665,500 | 270,000 | 135.3 154.0 53 |
| 8 | 1,2-bis(2,7-di-t-butylfluorenyl)ethane $ZrCl_2$ | 613,000 | 93,000 | 130.1 199.7 68 |
| 9 | 1-(4-benzylfluorenyl)-2-fluorenylethane $ZrCl_2$ | 561,000 | 510,000 | 129.6 131.2 45 |
| 10 | 1,2-bis(4,5-benzofluorenyl)ethane $ZrCl_2$ | 485,000 | 570,000 | 142.2 147.1 50 |
| 11 | 1,2-bis(fluorenyl)ethane $ZrCl_2$ | 420,000 | 620,000 | 140.6 159.5 55 |
| 12 | 1,2-bis(2-naphthyl-fluorenyl)ethane $ZrCl_2$ | 374,500 | 510,000 | 135.7 149.8 51 |
| 13 | 1-(4,5-benzofluorenyl)-2-fluorenylethane $ZrCl_2$ | 278,500 | 1,050,000 | 138.2 158.3 54 |
| 14 | 1,2-bis(1-methyl-fluorenyl)ethane $ZrCl_2$ | 220,500 | 270,000 | 134.1 176.4 60 |
| 15 | 1,2-bis(2-methyl-fluorenyl)ethane $ZrCl_2$ | 217,000 | 610,000 | 140.0 192.7 66 |
| 16 | 1,2-bis(2,7-dimethyl-fluorenyl) ethane $ZrCl_2$ | 213,500 | 680,000 | 143.8 172.8 59 |
| 17 | 1-(1,8-dimethylfluorenyl)-2-fluorenylethane $ZrCl_2$ | 209,700 | 200,000 | 135.6 (128.4) — |
| 18 | 1,2-bis(2,7-diethylfluorenyl) ethane $ZrCl_2$ | 188,500 | 830,000 | 132.1 154.0 53 |
| 19 | 1-(2,7-dimethylfluorenyl)-2-fluorenylethane $ZrCl_2$ | 124,500 | 575,000 | 132.0 149.8 51 |

In the above table the value for fusion enthalpy is in parenthesis in run 17 because of uncertainty in the result. To evaluate the results it is useful to compare the various metallocenes to the prior art metallocene of Run 11 which contains two unsubstituted fluorenyl groups. The substituted fluorenyl-containing metallocenes of Runs 1–10 were more active than the control metallocene of Run 11. While the metallocene of Run 13 was less active than that of Run 11, the metallocene of Run 13 gave a polymer have unexpectedly higher molecular weight. Runs 12 and 14–19 demonstrate that other substituents or other locations of substituents result in catalysts that are not as active as the control metallocene of Run 11. The molecular weight distribution of the polymers of Runs 1–4, 7 and 14–16 were evaluated using GPC and the results indicated that the polymers all had relatively narrow molecular weight distributions. Runs 1–4 and 14 and $M_w M_n$'s in the range of about 2.16 to about 3.4. The $M_w/M_n$ for the polymers of Runs 15 and 16 were slightly broader, i.e. 3.99 to 5.56.

That which is claimed:

1. A process for polymerizing at least one olefin comprising contacting said at least one olefin with a catalyst system produced by combining a metallocene and a suitable cocatalyst, said metallocene being selected from bridged metallocenes of Group IVB metals having two fluorenyl components bonded at the 9-position to opposite ends of an ethylene bridge further characterized by the fact that at least one of the fluorenyl group is substituted by a substituent selected from the group consisting of (1) a substituent in the 4-position selected from the group consisting of alkyl, aryl, and aralkyl radicals having 1 to 10 carbon atoms; (2) aryl substituents at the 2- and 7-positions; (3) tertiary butyl substituents at the 2- and 7-positions; and (4) a 4,5-benzo substituent.

2. A process according to claim 1 wherein said cocatalyst comprises an alkylaluminoxane.

3. A process according to claim 1 wherein the catalyst system includes 1,2-bis(2,7-dinaphthylfluorenyl) ethane zirconium dichloride.

4. A process according to claim 2 wherein the catalyst system includes 1,2-bis(4,5-dimethylfluorenyl) ethane zirconium dichloride.

5. A process according to claim 2 wherein said catalyst system includes 1,2-bis(4-methylfluorenyl) ethane zirconium dichloride.

6. A process according to claim 2 wherein said catalyst system includes 1-(4,5-dimethylfluorenyl)-2-(fluorenyl) ethane zirconium dichloride.

7. A process according to claim 2 wherein said catalyst system includes 1,2-bis(4-benzylfluorenyl) ethane zirconium dichloride.

8. A process according to claim 2 wherein said catalyst system includes 1-(4-benzylfluorenyl)-2-(fluorenyl) ethane zirconium dichloride.

9. A process according to claim 2 wherein said catalyst system includes 1-(2,7-dinaphthylfluorenyl)-2-(fluorenyl) ethane zirconium dichloride.

10. A process according to claim 2 wherein said catalyst system includes 1,2-bis(4,5-benzofluorenyl) ethane zirconium dichloride.

11. A process according to claim 2 wherein said catalyst system includes 1-(4,5-benzofluorenyl)-2-(fluorenyl) ethane zirconium dichloride.

12. A process according to claim 2 wherein said catalyst system includes 1,2-bis(2,7-di-tertiary-butylfluorenyl) ethane zirconium dichloride.

13. A process according to claim 2 wherein said catalyst system includes 1-(2,7-di-tertiary-butylfluorenyl)-2-(fluorenyl) ethane zirconium dichloride.

14. A process according to claim 2 wherein said polymerization is conducted under particle form polymerization conditions.

15. A process according to claim 14 wherein ethylene is the sole monomer employed.

16. A process according to claim 2 wherein said polymerization is conducted under solution polymerization conditions wherein the polymer that is formed is dissolved in the polymerization diluent.

17. A process according to claim 16 wherein ethylene is the sole monomer employed.

18. A catalyst system suitable for the polymerization of olefins, produced by combining a metallocene and a suitable cocatalyst, said metallocene being selected from bridged metallocenes of Group IVB metals having two fluorenyl components bonded at the 9-position to opposite ends of an ethylene bridge further characterized by the fact that at least one of the fluorenyl group is substituted by a substituent selected from the group consisting of (1) a substituent in the 4-position selected from the group consisting of alkyl, aryl, and aralkyl radicals having 1 to 10 carbon atoms; (2) aryl substituents at the 2- and 7-positions; (3) tertiary butyl substituents at the 2- and 7-positions; and (4) a 4,5-benzo substituent.

* * * * *